United States Patent [19]

Sawai et al.

[11] 4,118,192

[45] Oct. 3, 1978

[54] METHOD AND APPARATUS FOR THE MEASUREMENT OF ANTIGENS AND ANTIBODIES

[75] Inventors: Masanobu Sawai, Yamato; Tadamitsu Sudo, Sagamihara; Shogo Enomoto, Tokorozawa, all of Japan

[73] Assignee: Mitsubishi Chemical Industries Limited, Tokyo, Japan

[21] Appl. No.: 825,160

[22] Filed: Aug. 16, 1977

[30] Foreign Application Priority Data

Aug. 16, 1976 [JP] Japan .................................. 51-97158

[51] Int. Cl.² ...................... G01N 21/24; G01N 33/16
[52] U.S. Cl. ............... 424/12; 195/103.5 A; 356/246; 422/55; 422/56; 23/230 B
[58] Field of Search .................. 23/230 B, 253 R; 424/12; 356/105, 246; 195/103.5 A

[56] References Cited

U.S. PATENT DOCUMENTS

| 3,984,533 | 10/1976 | Uzgiris | 23/230 B |
| 4,011,044 | 3/1977 | Uzgiris | 23/230 B |

OTHER PUBLICATIONS

R. J. Cohen, Immunochemistry, 12, pp. 349-351, (Apr. 1975).

Primary Examiner—R.E. Serwin
Attorney, Agent, or Firm—Oblon, Fisher, Spivak, McClelland & Maier

[57] ABSTRACT

A method of the quantitative measurement of antigens and antibodies by reacting antibody- or antigen-sensitized insoluble carrier particles with a corresponding antigen or antibody or a mixture thereof in a sample and irradiating the reaction mixture with light of a specific wavelength to measure the absorbance of the reaction mixture, and an apparatus for use therein.

33 Claims, 12 Drawing Figures

METHOD AND APPARATUS FOR THE MEASUREMENT OF ANTIGENS AND ANTIBODIES

BACKGROUND OF THE INVENTION

1. Field of the Invention:

This invention relates to a method and apparatus for the measurement of antigens and antibodies. More particularly, this invention relates to a method of the quantitative measurement of antigens and antibodies by supporting an antibody or an antigen on insoluble carrier particles having minute particle diameters to sensitize the insoluble carrier particles, then reacting the sensitized carrier with a corresponding antigen, antibody or mixture thereof and irradiating the reaction mixture with light of a specific wavelength to measure the absorbance of the reaction mixture, and an apparatus for use therein.

2. Description of the Prior Art:

There is a continuing need for rapid, accurate, qualitative and quantitative determinations of biologically active substances, e.g., antigens, antibodies, at extremely low concentrations. Today, there is a wide need for determining the presence of drugs in body fluids. In addition, in medical diagnosis, it is frequently important to know the presence of various substances which are synthesized naturally by the body or ingested.

Heretofore it has been known to detect antibodies or antigens semiquantitatively by reacting latex particles on which an antibody or an antigen is supported with a corresponding antigen or antibody on a glass plate and observing visually the agglutination state.

In recent years, it was proposed in the following articles to quantitatively determine antigens and antibodies using the above-mentioned latex particles by supporting an antibody or an antigen on the latex particles, reacting the supported antibody or antigen with a corresponding antigen or antibody to agglutinate the latex particles, and measuring the rate of decrease in turbidity of the supernatant of the latex by means of visible rays for the determination of the antigen or antibody utilizing the agglutination phenomena of the latex reagent:

(A) CROATICA CHEMICA ACTA, 42, (1970), p.p. 457–466; and (B) European Journal of Biochemistry, Vol. 20, No. 4, (1971), p.p. 558–560.

Since the method of the above proposal utilizes the measurement of rate of decrease in turbidity to determine the antigen or antibody, it is necessary to use an antibody- or antigen-sensitized latex of an extremely low concentration, for example, in the range of 0.007 to 0.028%, to carry out the reaction of the latex and the antigen or antibody in a stationary state, to remove any impurity capable of affecting the turbidity from the sample, and the like. As a result, the above-mentioned method is disadvantageous in that the rate of the antigen-antibody reaction is inevitably decreased, both the precision and the reproducibility are inadequate for the determination technique for antigens or antibodies, and that the removal of impurities sometimes requires extremely complicated operations. Accordingly it is difficult to apply the above method to the determination of such antigen as fibrinogen (Fg), human chorionic gonadotropin (hCG) or the like which requires complicated procedures for the preparation of its reagent and which is difficult to cause reproducible agglutination reaction of said substance contained in blood or urine which also contains various other substances capable of adversely affecting the reaction.

Also in the following article, (C) Immunochemistry, Vol. 12, p.p. 349–351 (1975) it was proposed to determine quantitatively antibodies or antigens by irradiating the above-mentioned agglutinated latex particles with a laser beam and measuring the change in breadth of spectral lines of the scattered light of the laser beam in order to determine the mean diffusion constant (D) which gives an indication of the Brownian motion of the agglutinated particles which in turns is inversely proportional to the size of the agglutinated particles.

Also in this method, since the antibody- or antigen-sensitized latex is used in an extremely low concentration, for example, as low as 0.001%, the rate of the antigen-antibody reaction is so decreased that both the precision and the reproducibility become poor. In addition, this method is also disadvantageous in that it requires complicated calculation using the technique of spectrum analysis which in turn requires complicated operations, and that any impurity in the sample must be removed prior to the measurement. Accordingly, this method also has not been put into practice. The above paper C also describes that determination by the turbidity method as reported in the foregoing paper A gives extremely imprecise results (FIG. 2 on page 850 of the same).

SUMMARY OF THE INVENTION

Accordingly, it is an object of the invention to provide a method and apparatus for the rapid determination of an antibody and/or an antigen in a sample to be tested with high precision and good reproducibility.

It is another object of this invention to provide a method and apparatus for rapidly detecting whether the concentration of an antibody or antigen in a sample is higher or lower than a certain level, using an extremely small amount of the sample.

It is a still another object of this invention to provide a method and apparatus for determining an extremely slight amount of an antigen and/or an antibody, which could heretofore be determined practically only by radioimmunoassay (RIA), with a precision equal to that of RIA and much more rapidly and safely.

It is a further object of this invention to provide a method for the quantitative measurement of antigens capable of determining not only multivalent antigens but incomplete antigens such as, for example, haptens.

It is a still further object of this invention to provide a method for determining antibodies and/or antigens using not only the agglutination of the antibodies and/or antigens but the inhibitory actions thereof.

Briefly, these and other objects of this invention, as will hereinafter be made clear from the ensuring discussion, have been attained by supporting an antibody or an antigen on insoluble carrier particles with an average diameter of not greater than 1.6 microns to sensitize the insoluble carrier particles, reacting the supported antibody and/or antigen with a corresponding antigen or antibody or a mixture thereof in a liquid medium and irradiating the resulting reaction mixture with light having a wavelength in the range of 0.6 to 2.4 microns and longer than the average diameter of said carrier particles by a factor of at least 1.5 to measure the absorbance of the reaction mixture.

Figure 4:
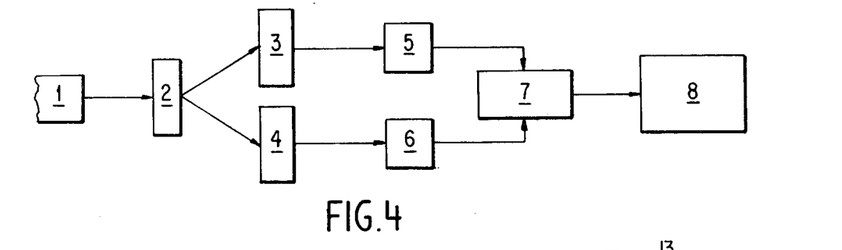
FIG. 4 is a systematic diagram which illustrates the basic structure of the apparatus for use in the invention.

In FIG. 4, figure 1 denotes a light source, 2 a filter, 3 a sample cell, 4 a compensatory cell, 5 and 6 filters, 7 an amplifier and 8 a recorder.

DETAILED DESCRIPTION OF THE PREFERRED EMBODIMENTS

As previously described, the prior art method wherein the degree of agglutination which is caused by bringing antibody- or antigen-sensitized latex particles into contact with a sample containing an antigen or an antibody is measured by the rate of decrease in turbidity of the supernatant of the latex, involves various disadvantages such as poor precision and reproducibility, since the reaction has to be carried out in a stationary state with an extremely dilute latex. Also in this prior art method, it is necessary to previously remove any impurity in the sample which may affect the turbidity.

Thus, it is a matter of course that in order to determine an antigen and/or an antibody in a sample with high precision and good reproducibility, an insoluble antibody- or antigen-sensitized carrier, for example, latex particles at as high a concentration as possible should desirably be brought into contact with the sample which contains the antigen and/or antibody capable of reacting with the supported antibody or antigen and in order to accelerate the antigen-antibody reaction caused thereby, this reaction should desirably be carried out under agitation, not in a stationary state.

We have now found that, in order to carry out an antigen-antibody reaction between an antibody or antigen supported on insoluble carrier particles at as high a concentration as possible and a corresponding antigen or antibody in a sample under non-stationary conditions and at the same time to detect quantitatively the degree of this reaction, it is remarkably effective:

(1) to use an insoluble carrier having an average particle diameter of not greater than 1.6 microns, (2) to irradiate the antigen-antibody reaction mixture with light having a wavelength in the range of 0.6 to 2.4 microns and longer than the average diameter of the carrier particles by a factor of at least 1.5; and (3) to measure the intensity of the transmitted light. The reason is that the degree of the antigen-antibody reaction in the presence of the sensitized insoluble carrier particles corresponds very closely to the intensity of the transmitted light. It is apparent that the degree of the antigen-antibody reaction also corresponds to the amount (or concentration) of the antibody and/or antigen in the sample as long as the reaction is carried out under specifically determined conditions. The above-mentioned method according to this invention, therefore, enables rapid determination of an antibody and/or antigen in a sample with an extremely high precision by a technique quite different from the measurement of turbidity or means diffusion constant as in the prior art methods.

The light of wavelengths in the range of 0.6 to 2.4 microns which are used in this invention are those in the near infrared region or in a portion of the visible region which is closely adjacent to the near infrared region.

Of these regions, in accordance with the invention, it is preferred to use a ray in the near infrared region of 0.8 to 1.8 microns, more preferably 1 to 1.4 microns.

Heretofore the technique of spectrum analysis using a ray in the infrared region of wavelengths of at least 2.5 microns or a ray in the ultraviolet region of wavelengths of not greater than 0.4 micron is known as one method for investigating molecular structures of characteristics thereof. The rays in the near infrared or the adjacent visible region which is used in this invention and which may hereinafter be referred to as "rays in the near infrared regions" for the sake of convenience, however, have heretofore been considered to have only limited uses and therefore attracted little attention.

According to our investigation, it has been found that the above-mentioned rays in the near infrared region in principle possess eligibility as the light to be used in this invention, since they are transmitted very well by aqueous media such as water, aqueous solutions and the like which are used most generally as the basal media for the antigen- or antibody-containing samples such as water, sera, urine, salt solutions, etc., as well as, as the basal media for the above-mentioned latices and particularly the rays in the near infrared ranges of 0.8 to 1.4 microns and 1.53 to 1.88 microns are absorbed by the aqueous media only to a very little extent. In addition it has been found that, when the reaction mixture obtained by reacting the foregoing antibody- or antigen-sensitized insoluble carrier particles having an average diameter of not greater than 1.6 microns, preferably 0.1 to 1 micron with the antigen and/or antibody in the sample to cause agglutination is irradiated with a light in the above-mentioned near infrared region having a wavelength longer than the average diameter of the carrier by a factor of at least 1.5, preferably at least 2 in accordance with the invention, the intensity of the light transmitted from the reaction mixture corresponds very closely to the degree of the agglutination resulting from the antigen-antibody reaction.

The transmittance of the above-mentioned ray as used herein corresponds to the absorbance (A) which can be determined by means of spectrophotometers such as, for example, those generally used for the infrared spectrometry, and therefore it may be expressed in terms of such absorbance for the sake of convenience.

In the infrared spectrometry, the above absorbance (A) is represented by the formula:

$$A = \log (I_o)/(I)$$

where Io is the intensity of the transmitted light when the cell contains only the solvent, and I is that when the cell contains a solution of a certain concentration. Accordingly, the above-mentioned transmittance as used herein is hereinafter referred to as "absorbance (A)" for the sake of convenience.

In accordance with the invention, the determination of absorbance A may be performed with a spectrophotometer similar to that used in the near infrared spectrometry using a ray in the above-mentioned near infrared region and using the above formula, wherein Io represents the intensity of the transmitted light of the applied ray in the above-mentioned near infrared region when the cell contains a mixture of an antibody- or antigen-sensitized insoluble carrier particles or a suspension containing the carrier and the basal medium of a sample; and I represents the intensity of the transmitted light of the same applied ray in the above-mentioned near infrared region when the cell contains the reaction mixture of the suspension containing the antibody- or antigen-sensitized insoluble carrier particles and the sample containing an antigen and/or an antibody.

In brief the above-mentioned absorbance (A) relates to the relative ratio of Io/I. If the basal medium of the sample is a transparent liquid medium, the measurement of Io may conveniently be performed with only the suspension containing the antibody- or antigen-sensitized insoluble carrier particles, said suspension having been diluted with, for example, water to the same concentration as that in the mixture.

Figure 1:
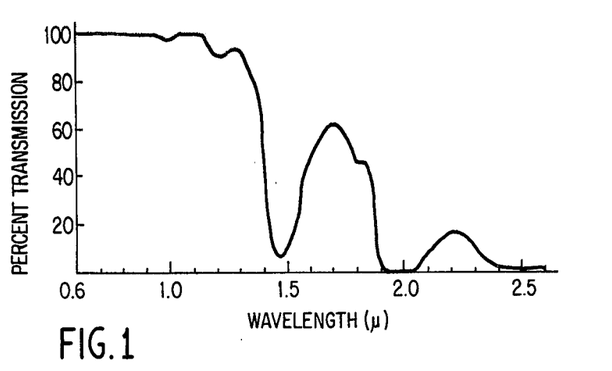
FIG. 1 is a chart of the absorption spectra of water measured at wavelengths of the applied light in the range of 0.6 to 2.4 microns using an absorption cell with a thickness of 1 mm.

For example, percent transmission spectrum in the range of 0.6 to 2.4 microns of a water layer 1 mm in thickness is shown in FIG. 1, wherein the abscissa indicates the wavelength of light and the ordinate the percent transmission of the light. It can be seen from FIG. 1 that the rays of wavelengths in the range of 0.6 to 1.4 microns are transmitted by water without substantial absorption by the water which is employed most widely as the basal media for latices and samples, and that the rays of wavelengths in the range of 1.53 to 1.88 microns are also considerably transmitted by water so that the light of wavelengths in those ranges can be utilized in principle in accordance with the invention. Also, it is apparent from FIG. 1 that the rays of wavelengths in the range of 2.1 to 2.35 microns are also transmitted by water in the order of 20%, and therefore it should be understood that the rays of such wavelengths can be used in conjunction with a highly sensitive photometer, although they are rather not preferred.

Figure 2:
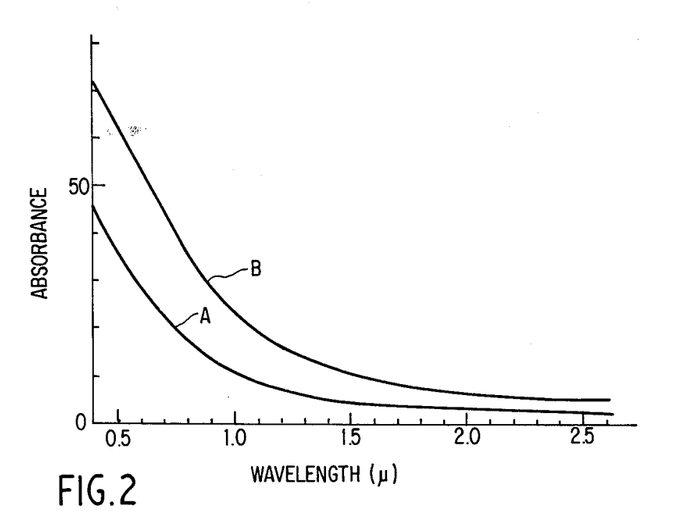
FIG. 2 is a graph which shows the change of absorbance with particle diameter of polystyrene latex.

FIG. 2 shows the relationship between the absorbance of a polystyrene latex (1% solids content by weight) in the ordinate and the wavelength of light in microns in the abscissa when a cell in 2 mm thickness is used. In FIG. 2, Curve A denotes the change in absorbance of a polystyrene latex in which the average diameter of the particles is 0.481 micron and Curve B denotes that of a polystyrene latex in which the average diameter is 0.804 micron. In the determination of absorbance, the latex is diluted for the convenience of the measurement, and the value obtained by multiplying the observed absorbance by the dilution factor is regarded as the absorbance of the latex.

As will be understood from FIG. 2, the absorbance of the latex is so significantly increased with the rays of wavelengths less than 0.6 micron that it is quite difficult to measure the change in the foregoing light transmittance of an antigen-antibody reaction mixture using a ray of such a wavelength, whereas with the rays of wavelengths of at least 0.8 micron, particularly at least 1 micron, the absorbance of the latex itself is relatively small so that the light of wavelengths of at least 0.8 micron, preferably at least 1 micron are suitable for the above-mentioned measurement of light transmittance.

When Curve A is compared with Curve B in FIG. 2, it is recognized that the absorbance of the latex increases with increasing average diameter of the polystyrene latex particles. Accordingly it would also be understood that those latex particles having an excessively large average diameter are not useful for this invention.

In accordance with our investigation, it has been found that the insoluble carrier particles useful for this invention must have an average particle diameter of not greater than 1.6 microns and that those latex particles having an average diameter of 0.1 to 1 micron, more preferably 0.2 to 0.8 micron are preferred.

Figure 3:
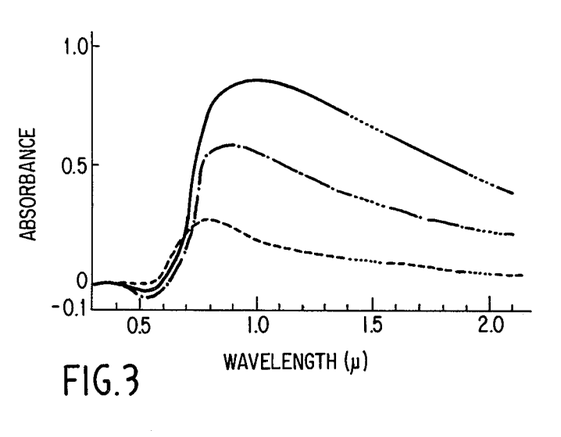
FIG. 3 is a graph which shows the change of absorbance with reaction time of an antigen-antibody reaction.

FIG. 3 shows the relationship between the change in absorbance of an antigen-antibody reaction mixture in the ordinate and the wavelength of light in microns in the abscissa at various reaction time when the antigen-antibody reaction is carried out in exactly the same manner as in Example 1 except that a polystyrene latex with an average particle diameter of 0.234 micron is used. In FIG. 3, Curves C, D and E denote the absorbance of the reaction mixture after the antigen-antibody reaction is carried out for 3, 10 and 20 minutes, respectively.

As can be seen from FIG. 3, when the absorbance of the antigen-antibody reaction mixture is determined with a ray of a wavelength less than 0.6 micron, in the wavelength region of about 0.6 to 0.4 $\mu$ the degree of the reaction (i.e., the reaction time) does not correspond to the absorbance, and in the wavelength region of not greater than about 0.4 micron the absorbance does not appreciably vary with the degree of the reaction. On the other hand, with a ray of a wavelength of at least about 0.75 micron, the absorbance of the reaction mixture gives a significantly good correlation with the reaction time or degree of the reaction. The dotted line sections in Curves C, D and E in FIG. 3 indicate that in these wavelength regions the absorbance cannot be determined accurately even with an increased slit width, since the absorption by water is much high in these regions.

As can be seen hereinafter from Example 4, when a polystyrene latex having an average particle diameter of 0.804 micron is used, a good correlation is established between the absorbance of the antigen-antibody reaction mixture and the concentration of the antigen using a light of a wavelength longer than said average diameter by a factor of at least about 1.5, e.g., a wavelength of about 1.2 microns, as long as the concentration of the antigen in a sample is not greater than $0.6\mu$ g/ml ($0.6 \times 10^{-6}$ g/l). In this case, therefore, the quantitative measurement according to the invention can be performed by irradation with a light having a wavelength of 1.2 microns or longer.

In the case of those latex particles having a relatively small average diameter, however, as can be seen from FIG. 3, it is advantageous to use a near infrared ray having a wavelength in the range of about 0.8 to 1.4 microns, preferably 1 to 1.4 microns and longer than the average diameter of the carrier by a factor of at least 2.

In accordance with one embodiment of this invention, it is desirable to irradiate a reaction mixture of a carrier of a specific particle size on which a particular antibody or antigen is supported and a particular antigen or antibody or a mixture thereof in a test liquid with light of an appropriate wavelength in the range of 0.6 to 2.4 microns in order to preliminarily detect a wavelength region of applied rays in which a quantitative correlation is established between the change in concentration of the particular antigen or antibody or a mixture thereof (including the reaction product) in the test liquid and the absorbance of the reaction mixture, and subsequently to apply light of a specific wavelength in this region for the determination of absorbance.

Thus, in accordance with the invention, it is possible to determine the amount or concentration of an antigen and/or an antibody in a sample by using insoluble carrier particles having an average diameter of not greater than 1.6 microns, preferably in the range of 0.1 to 1.0 micron, more preferably 0.2 to 0.8 micron and most preferably in the range of 0.3 to 0.6 micron, supporting an antibody or an antigen on the carrier (i.e., sensitizing the carrier with the antibody or antigen), reacting the sensitized carrier with the antigen and/or antibody in the sample, and determining the absorbance of the reaction mixture with light of a wavelength in the range of 0.6 to 2.4 microns, preferably 0.6 to 1.8 microns, more preferably 0.8 to 1.4 microns and most preferably 1 to 1.4 microns. As previously mentioned, the light to be applied should have a wavelength longer than the average diameter of the insoluble carrier particles by a factor of at least 1.5, preferably at least 2, and more preferably at least 2.5.

The insoluble carrier particles useful for this invention include those organic polymer microparticles which are substantially insoluble in the particular liquid medium used for the measurement according to the invention and which have an average diameter within the above-mentioned range, such as, for example, latices of organic polymers such as polystyrene and styrene-butadiene copolymer obtained by emulsion polymerization; dispersed coccal bacteria such as staphylococci and streptococci, Bacillus prodigiosus, rickettsia, cell membrane fragments, etc.; as well as microparticles of inorganic oxides such as silica, silica-alumina and alumina, and finely pulverized minerals, metals and the like.

In accordance with the invention, an antibody or an antigen which is reactive with the antigen and/or antibody in the sample to be measured is supported on the above-mentioned insoluble carrier particles such as, for example, latex particles (i.e., to sensitize the carrier). For this purpose, the antibody or antigen may be physically and/or chemically adsorbed on the carrier.

Antibodies consist of proteins, whereas antigens are composed of one member selected from various substances such as, for example, proteins, polypeptides, steroids, polysaccharides, lipids, pollen, dust and the like. There have already been proposed a number of methods for supporting these antibodies or antigens, particularly antibodies on insoluble carrier particles.

When an incomplete antigen, particularly a hapten is supported on insoluble carriers, it is advantageous to chemically modify the carriers with, for example, a coupling agent and subsequently bind the antigen chemically to the modified carriers.

Contrary to the known prior art methods which utilize the measurement of turbidity or the measurement of mean diffusion constant with a laser beam, the method according to this invention provides conditions that enable the insoluble carrier particles sensitized with an antibody or an antigen to react with a corresponding antigen and/or antibody as actively as possible.

On this account, in accordance with the invention, the insoluble carrier particles, for example, latex particles, which are sensitized with an antibody or an antigen (hereinafter referred to as "sensitized carrier particles") may be used as a suspension having a concentration of not less than 0.05% by weight, preferably in the range of 0.1 to 1%, more preferably 0.2 to 0.6%. When the concentration of the sensitized carrier particles is much too high, as is apparent from FIG. 2, the transmittance of the suspension itself is so decreased that the measurement of absorbance according to the invention is made difficult. However, in the concentration range in which such a measurement of absorbance is possible, higher concentration of the sensitized carrier particles in the suspension is preferred, whereby it is possible to increase the sensitivity of the quantitative measurement of antigens and antibodies.

In accordance with the invention, also contrary to the prior art methods, the sensitized carrier particles and the antigen- and/or antibody-containing sample are reacted under non-stationary or non-standing conditions.

For this purpose, the reaction may be advantageously carried out under agitation. Since the reaction is generally carried out in a thin cell, the agitation is conveniently effected for example, by moving a rod vertically or transversely in the cell. Of course, the sensitized carrier particles and the sample may be reacted outside the cell for a certain period of time under specifically determined conditions and thereafter the reaction mixture is placed in the cell for the measurement of absorbance. However, in order to make the reaction conditions reproducible, particularly with respect to reaction time, in every measurement, the sensitized carrier particles and the sample may be reacted under specifically determined conditions directly in a cell which has been set in a spectrophotometer, whereby more accurate determination can be achieved by measuring the absorbance immediately after a prescribed period of reaction time or by measuring the time required to reach a predetermined value of absorbance while the reaction is continued under specifically determined conditions.

Thus, the present invention not only makes it possible to determine such a concentration of an antigen and/or an antibody in a sample that could heretofore be observed visually in a semiquantitative manner, but enables the determination of an antigen and/or an antibody in such a trace amount that could heretofore be determined only by radioimmunoassay (RIA), with a precision equivalent to that of the RIA method.

In order to determine an antigen and/or an antibody in a sample containing an unknown amount of the antigen and/or antibody in accordance with the invention, a set of dilute standard samples are prepared from a standard sample containing a definite amount of the corresponding antigen and/or antibody by diluting it by various factors. Each of the dilute and undiluted standard samples may be reacted under predetermined conditions with insoluble carrier particles sensitized with a definite amount of a corresponding antibody or antigen in accordance with the invention, and the absorbance of each reaction mixture is determined to prepare a standard curve for the particular combination of the antigen and/or antibody with the sensitized carrier particles, which indicates the relationship between the amount (concentration) of the antigen or antibody and the absorbance (this type of standard curve being hereinafter referred to as "Standard Curve A" for convenience). Subsequently, an unknown sample to be tested is reacted with the same sensitized carrier particles as that used in the preparation of the standard curve under substantially the same conditions as in the preparation of the standard curve, and the absorbance of the reaction mixture is measured. The amount (or concentration) of the corresponding antigen and/or antibody in the unknown sample can be determined by comparing the value of absorbance thus obtained with Standard Curve A.

Alternatively, in the preparation of a standard curve like that described in the above, such a standard curve may be prepared that indicates the relationship between the amount (or concentration) of the antigen or antibody in the standard sample used and the reaction time required to reach a predetermined value of absorbance (this type of standard curve being hereinafter referred to as "Standard Curve B" for convenience). Also in this case, when an unknown sample is reacted with the same sensitized carrier particles under substantially the same conditions as in the preparation of the standard curve, the amount (or concentration) of the antigen and/or antibody in the unknown sample can be determined by reading the time required to reach the predetermined value of absorbance.

Thus, in accordance with the invention, the amount of concentration of an antigen and/or an antibody in an unknown sample may be determined by way of, either (A) the measurement of absorbance of the unknown sample (using Standard Curve A for calibration), or (B) the measurement of the rate of reaction, or the reaction time required for the absorbance to reach a prescribed value (using Standard Curve B for calibration).

As described previously, the above method (A) is suitable as a determination system with a significantly high precision, not only when the concentration of an antigen and/or an antibody in an unknown sample is relatively high, but even if it is so low that it could heretofore be determined only by the RIA method. On the other hand, the above method (B) wherein the reaction rate is measured is suitable for determining a relatively large amount (concentration) of an antigen and/or an antibody in an unknown sample, but it is advantageous in that the measurement is quite simple. According to our investigation, Standard Curve A as described above gives generally a gentle S-shaped curve rather than a straight line, but no disadvantageous effect is found on the precision of the determination.

The reason why the curve assumes the S-shape as described above is presumed by us to be that the rate of reaction takes part in this shape at lower concentrations of the antigen and/or antibody, whereas the saturation of active sites in the carrier takes part at higher concentrations. It is possible, of course, to enlarge the linear portion in the S-shaped curve by selecting the conditions appropriately in the preparation of the standard curve, and apply substantially only this portion to the determination of unknown samples.

As stated above, the present invention is characterized in that sensitized carrier particles at as high a concentration as possible may be contacted and reacted with a sample. Therefore, the cell for use in measuring the absorbance of the reaction mixture should have a thickness less than that of a cell for use in visible spectrum analysis, and, for example, those cells having thickness in the range of 0.5 to 4 mm, particularly 1 to 2.5 mm are preferred.

In order to effect a highly sensitive determination of a trace amount of an antigen or an antibody which has heretofore been subjected to the RIA method, it is particularly advantageous:

(a) to use an antigen or antibody having as high an equilibrium constant as possible, (b) to use latex particles, particularly with an average diameter of 0.3 to 0.6 micron, the size distribution of which should be as narrow as possible, (c) to determine the absorbance with light of a wavelength of 1.2 to 1.4 microns, (d) to select a relatively long reaction time, for example, in the range of 1 to 3 hours, and (e) to increase the concentration of the sensitized latex carrier as long as the absorbance is measurable.

Also, in order to determine an unknown sample accurately in a relatively short time by the measurement of reaction rate (using Standard Curve B), it is advantageous, (f) to use latex particles having a relatively large average diameter, (g) to increase the concentration of the carrier particles in the latex as long as the measurement of absorbance is possible, and (h) to make the period of reaction time relatively short, for example, in the range of 5 seconds to 10 minutes, preferably 10 seconds to 3 minutes.

In this case, when the time required for the absorbance to reach a predetermined value is plotted as the ordinate and the concentration as the abscissa, both on a log scale, the resulting Standard Curve B will give a straight line to advantage.

The present invention is described in the above with respect to the determination of an antigen and/or an antibody in a sample by applying the agglutination of the antigen and/or antibody in the sample with sensitized carrier particles (i.e., LA system).

The method according to the invention is also suitable for the determination of a sample to which the inhibitory action against the above-mentioned agglutination is applied (i.e., LI system).

Incomplete antigens such as, for example, haptens can be determined by applying the method according to the invention to the LI system.

In this case, for instance, an antigen may be supported on the insoluble carrier particles as used in this invention, the sensitized carrier particles are reacted competitively with a given amount of an antibody which has been reacted with an antigen of a predetermined concentration (i.e., a standard antigen solution), and the absorbance of the resulting reaction mixture is determined. The above procedure is repeated at various concentrations of the standard antigen liquid to prepare Standard Curve C. Subsequently, an unknown sample is reacted with the same antibody of a definite concentration, and the resulting reaction mixture is then reacted with the sensitized carrier. These reactions should be carried out under substantially the same conditions as in the preparation of Standard Curve C. The absorbance of the final reaction mixture with the sensitized carrier particles thus obtained is determined and compared with the standard curve (C) to determine the amount (concentration) of antigen in the unknown sample.

Following the procedure of the above-mentioned LI system except that a certain antibody is supported on the insoluble carrier particles, an antibody in an unknown sample can be determined by the LI system. In addition, it is possible, if desired, to support both an antigen and an antibody of different species on the insoluble carrier particles and determine an antigen and an antibody in an unknown sample. Thus, in accordance with the invention, the quantitative measurement of a wide variety of antigens and/or antibodies are possible, for example, (1) blood examination of subjects or blood donors which is indispensible for emergency operations, for example, detection of blood group substances, the Au- or HB- antigen or other contaminants in the blood, or determination of fibrin/fibrinogen degradation products (FDP) which is recently regarded as useful in the convalescent control for kidney transplantation or renal failure patients, (2) determination of human chorionic gonadotropin (hCG) which is regarded as significantly important in the pregnancy diagnosis or the convalescent control or chorioepithelioma, (3) determination of hCG, or urinary estriol glucuronide which is a metabolite of follicular hormone, said determination being required for monitoring pregnancy, (4) determination of oxytocin in blood which is considered to be a uterine contraction inducer, (5) determination of certain adrenal cortical hormones such as corticoids and aldosterone, or adrenocorticotropic hormones (ACTH), (6) determination of insulin for diabetics, or determination of follicle stimulating hormone, luteinizing hormone, estrogens, corpus luteum hormone, etc., (7) determination of gastrin or secretin which is a gastrointestinal hormone, (8) detection and determination of an antibody in the body fluid of patients with allergy, syphilis, or hemolytic streptococcicosis, rubella, autoimmune diseases such as collagen disease and other infection diseases, and the like.

The present invention may be adopted, of course, for the qualitative or semi-quantitative measurement of these antigens and/or antibodies.

In accordance with another aspect of this invention, there is provided a novel apparatus for measuring antigens and antibodies which can be used in the above-mentioned method of this invention.

The apparatus according to the invention involves (a) insoluble carrier particles for supporting an antibody or an antigen, said carrier particles having an average diameter of not greater than 1.6 microns, (b) an absorption cell for holding a reaction mixture obtained by reacting the antibody or antigen supported on the insoluble carrier and a corresponding antigen and/or antibody in a liquid medium, said cell having a thickness in the range of 0.5 to 4 mm, and (c) a photometer equipped with an irradiation unit capable of applying a particular light ray in the wavelength range of 0.6 to 2.4 microns.

The measuring apparatus according to this invention may possess the same basic structure as in the prior art photometric apparatus, except for the essential structural characteristics as described in (a), (b) and (c).

Thus, as illustrated in FIG. 4, the basic structure of the apparaus according to the invention comprises an irradiation unit comprising light source 1 and filter or prism 2; sample cell 3 for holding a sample for the measurement of an antigen-antibody reaction, and reference cell 4 for holding a control sample for compensation; photocells 5 and 6 for sensing the light transmitted by the respective cells and transforming them into electric signals, amplifier 7 for amplifying the electric signals; and displaying or recording unit 8 for displaying or recording the amplified electric signals.

Light source 1 may be a conventional tungsten lamp and the light emitted from light source 1 is monochromatized through filter or prism 2 so as to apply a light beam of a specific wavelength in the range of 0.6 to 2.4 microns, preferably 0.8 to 1.4 microns and more preferably 1.0 to 1.4 microns to cells 4 and 5.

Filter or prism 2 is therefore selected from those capable of effectively monochromatizing the light of the above-mentioned wavelengths. For instance, an interference filter of 1,200 ± 50 millimicrons may be used as the filter or a quartz or glass prism as the prism.

The applying light thus monochromatized is converged appropriately through a slit or a lens before it is applied to sample cell 3 and reference cell 4.

Figure 5:
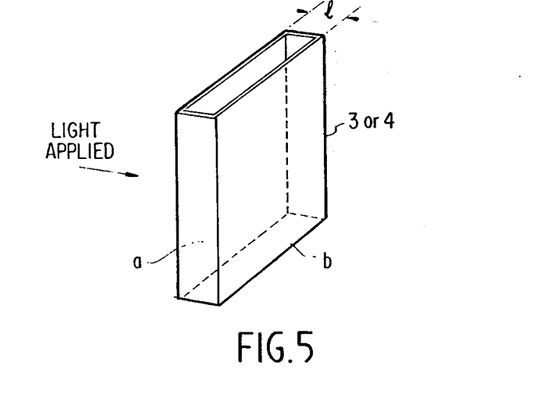
FIG. 5 is a perspective view of an absorption cell useful for both samples and controls.

The sample cell 3 and reference cell 4 may be composed of transparent glass or synthetic resin (e.g., acrylic resins) and may be a box-shape having a rectangular or oblong cross section (See FIG. 5). The cell thickness, that is, the distance ($l$) between walls (transmissive walls) a and b, respectively, or the side from which the light is applied and on the opposite side, may be in the range of 0.5 to 4 mm, preferably 1 to 2.5 mm. The transmissive walls may advantageously possess at least 30% transmission, preferably 80% or higher transmission, for the light of wavelengths in the range of 0.6 to 2.4 microns.

In sample cell 3 is placed a reaction mixture prepared by reacting an antigen and/or an antibody or a mixture thereof with a corresponding antibody or an antigen supported on an insoluble carrier particles in a liquid medium in such a manner as previously described with respect to the method of this invention. On the other hand, in reference cell 4 is placed a control sample comprising only the antibody or antigen supported on the insoluble carrier particles and dispersed in the liquid medium.

The light beams transmitted by cells 3 and 4, respectively, are received in photocells 5 and 6, respectively, and transformed into electric signals the respective strength of which is in proportion to the respective intensities of light received by the cells. Any type of photocells 5 and 6 may be used, as long as they function to transduce an intensity of light received into an electric signal having the strength proportional to the intensity of light. Lead sulfide photoconductive element, for example, may be employed to advantage.

The electric signals thus transformed by the photocells may be amplified by amplifier 7 in a conventional manner and displayed or recorded on indicator or recorder 8 so as to read them visually.

If a horological mechanism is incorporated in indicator or recorder 8, it is possible to automatically record the absorbance after a predetermined period of reaction time, or record the time required for the absorbance to reach a predetermined value.

In a preferred embodiment of the apparatus according to the invention, sample cell 3 is equipped with an agitator, which may be a mixing rod movable in the cell.

Figure 6:
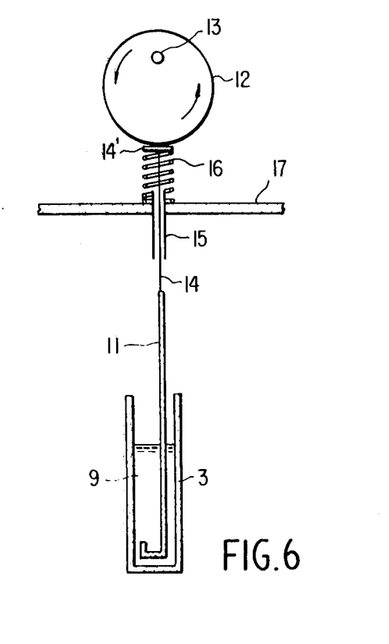
FIG. 6 is a schematic diagram of a stirring mechanism which may preferably be used in the practice of this invention.

FIG. 6 shows a preferred embodiment of the agitator mechanism for agitating mixture 9 of a sample and sensitized carrier particles (e.g., sensitized latex) which is held in sample cell 3 for use in the apparatus of the invention. Referring to FIG. 6, L-shaped mixing rod 11 can move up and down to agitate mixture 9 in cell 3 by the vertical up and down motion of T-shaped hammer-headed connecting rod 14, said connecting rod 14 being contacted at its upper flat plate 14' with rotary disc 12 which is driven by eccentric shaft 13. FIG. 17 indicates a light-shielding lid, and connecting rod 14 moves up and down through hollow tube 15 fixed to and through lid 17, wherein connecting rod 14 goes down with rotation of eccentric disc 12 and is then lifted by the restoring force of spring 16 which is provided between lid 17 and upper flat plate 14' of connecting rod 14.

When sample cell 3 to be used in the photometric apparatus as shown in FIG. 4 has such a structure, for example, as shown in FIG. 6, cell 3 can be placed in the dark which is shielded from sunlight and a mixture of a sample and sensitized carrier particles (sensitized latex) introduced in cell 3 can be mixed with L-shaped mixing rod 11 while being irradiated with a near infrared ray of a predetermined wavelength, whereby it is possible to agitate the mixture without obstruction to the light path of the near infrared ray. Thus, by use of the above-mentioned apparatus, the antigen-antibody reaction between the sample and the sensitized carrier particles can be accelerated, and in addition, it is possible to stop the reaction immediately after a predetermined period of reaction time has passed, accurately read the reaction time elapsed by the time the absorbance reaches a predetermined value, and the like.

Having generally described this invention, a more complete understanding can be obtained by reference to certain examples which are provided herein for purpose of illustration only and are not intended to be limiting in any manner.

EXAMPLE 1

(1) Preparation of an antifibrinogen antibody-sensitized latex (anti-Fg-latex) reagent To 10 ml of a glycine buffer solution of anti-human fibrinogen (Fg) antibody (2 mg/ml concentration), 1 ml of a polystyrene latex with an average particle diameter of 0.481 micron (Dow Chemical Co., 10% solids content by weight) is added, and the mixture is stirred at room temperature for 30 minutes, then warmed to 40° C and stirred for an additional 30 minutes at this temperature, and centrifuged (at 12,000 rpm) for 50 minutes with cooling at 2° to 4° C. The precipitate is separated by decantation and the collected anti-Fg antibody-sensitized latex particles are suspended in a bovine serum albumin solution (0.2 wt. % concentration) to prepare an anti-Fg-sensitized latex reagent containing the sensitized latex particles at a concentration of 1% by weight.

(2) Preparation of a standard curve A 0.1 ml aliquot of the anti-Fg-latex reagent as prepared in Part (1) is placed in a plastic test tube (7 mm inner diameter × 70 mm long) together with 0.3 ml of a standard fibrinogen (Fg) solutions (in an isotonic sodium chloride solutions containing 0.2% by weight bovine serum albumin) which contains Fg at a concentration indicated in Table-A below, and the mixture is shaken at room temperature for 20 minutes on a reciprocal shaker at 200 strokes per minute to effect the antigen-antibody reaction. Immediately thereafter, the reaction liquid in the test tube is transferred to a glass absorption cell having a thickness of 2 mm and the absorbance is determined at a wavelength of the applied light of 1.2 microns with an automatic recording spectrophotometer (Hitachi Ltd., Model EPS-3; using as a control a suspension of 0.1 ml of the anti-Fg-latex reagent diluted with 0.3 ml of the isotonic sodium chloride solution containing 0.2% by weight bovine serum albumin). The measurement is carried out twice with each standard Fg solution. The results are summarized in the following Table A.

Table - A

| Concentration of standard Fg solution (μg/ml) | Absorbance at 1.2μ | | |
|---|---|---|---|
| | First | Second | Mean |
| 0.1 | 0.336 | 0.363 | 0.350 |
| 0.2 | 0.836 | 0.778 | 0.807 |
| 0.3 | 1.083 | 1.167 | 1.125 |
| 0.4 | 1.330 | 1.333 | 1.332 |
| 0.5 | 1.403 | 1.430 | 1.417 |

Figure 7:
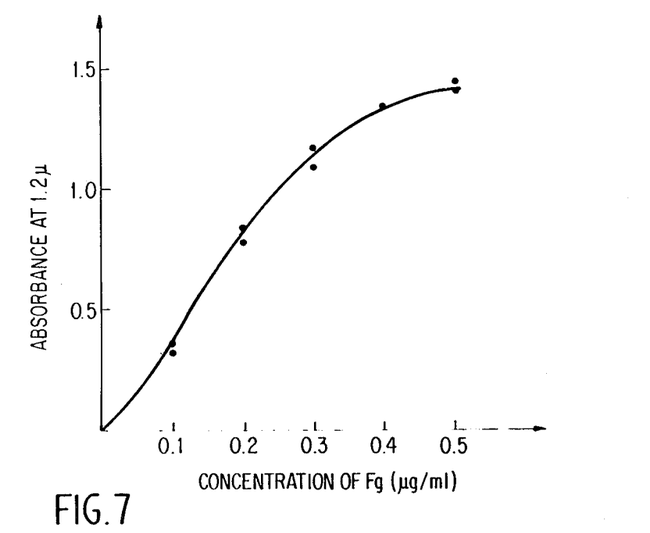
FIG. 7 shows a Fg standard curve at a wavelength of 1.2 microns using standard Fg solutions and anti-Fg-polystyrene latex particles with an average diameter of 0.481 micron.

When the above data are plotted graphically with concentration of standard Fg solution as abscissa and absorbance (mean value) at 1.2 microns (in wavelength of applied light) as ordinate, a standard curve as shown in FIG. 7 is obtained.

(3) Quantitative determination of Fg in unknown samples A sample of blood, urine or fluid in the thoracic cavity (intrapleural fluid) is collected from a subject and if the sample is blood, the serum or plasma is separated therefrom. A 0.3 ml aliquot of the sample or its diluted sample is treated with 0.1 ml of the anti-Fg-latex reagent as prepared in Part (1) in exactly the same manner as described in Part (2), and the absorbance is determined in the same manner as described in Part (2). Using the standard curve obtained in Part (2), the concentration of Fg corresponding to the value of absorbance is read and the results are summarized in Table-B below.

For the purpose of comparison, Table-B also involves the data obtained in accordance with the conventional radioimmunoassay (RIA) method (S. M. Ratkey, et al., Brit. J. Haematol. 30, 145–149, 1975) and slide method (Fujimaki, Tamura and Takahaski, Rinsho Kagaku (Clinical Science), Vol. 12, 507, 1976; and Fujimaki, Ikematsu, Takeuchi and Kato, Rinsho Byori (Japanese Journal of Clinical Pathology), 21, 973, 1973).

Table - B

| Subject No. | Unknown sample Material | dilution factor | Absorbance determined | Fg concentration in unknown sample (μg/ml) Method of this invention | RIA method | Slide method |
|---|---|---|---|---|---|---|
| 1 | Urine | × 2 | 0.764 | 0.402 | 0.359 | 0.5 |
| 2 | " | × 16 | 1.162 | 5.178 | 5.117 | 8.0 |
| 3 | " | × 1 | 1.233 | 0.347 | 0.368 | 0.5 |
| 4 | " | " | 0.090 | 0.021 | 0.024 | less than 0.5 |
| 5 | " | " | 0.011 | 0.003 | 0.006 | " |
| 6 | " | " | 0.175 | 0.042 | 0.037 | " |
| 7 | " | " | 0.066 | 0.016 | 0.011 | " |
| 8 | " | " | 0.171 | 0.041 | 0.008 | " |
| 9 | " | " | 0.020 | 0.005 | 0.007 | " |
| 10 | " | " | 0.199 | 0.048 | 0.072 | " |
| 11 | Serum | × 10 | 0.310 | 0.760 | 0.800 | 1.0 |
| 12 | " | " | 0.330 | 0.812 | 0.863 | 0.9 |
| 13 | " | " | 0.520 | 1.317 | 1.335 | 1.25 |
| 14 | " | " | 0.348 | 0.858 | 0.892 | 1.0 |
| 15 | Fg-Free plasma | " | 0.550 | 1.400 | 1.520 | 2.0 |
| 16 | Cancerous intrapleural fluid | × 640 | 1.210 | 217.12 | 197.4 | 320 |

From the above results, it can be seen that the data of Fg concentration obtained by the method of this invention are in significantly close agreement with those obtained by the RIA method which is known as the most precise determination method of the conventional method. The correlation coefficient between the method of this invention and the RIA method is 0.999.

EXAMPLE 2

An anti-Fg-sensitized latex reagent (containing 1% by weight latex particles) is prepared in the same manner as in Example 1, Part (1), except for use of another polystyrene latex having an average particle diameter of 0.234 micron (Dow Chemical Co., 10% solids content by weight).

A 0.1 ml aliquot of the anti-Fg-sensitized latex reagent thus obtained is mixed with 0.3 ml of a standard Fg solution (containing 0.5μg/l of Fg) and shaken at room temperature for 5 minutes on a reciprocal shaker at 250 strokes per minute to carry out the antigen-antibody reaction. Subsequently, the absorbance of the reaction mixture is determined at a wavelength of applied light of 1.2 microns in the same manner as described in Example 1, Part (2).

In order to confirm the reproducibility of the measurement, the same procedure is repeated three more times. The results are given in Table-C below.

Also, following the above-mentioned measuring test except for using serums which are isolated from blood samples collected from a patient instead of the standard Fg solutions, the same procedure as described above is repeated four times on different days to confirm the reproducibility of the measurement for the actual body fluid. The results are also given in the following Table-C.

Table - C

| Measurement No. | Absorbance Standard Fg solution | Serum |
|---|---|---|
| 1 | 0.582 | 0.294 |
| 2 | 0.565 | 0.280 |
| 3 | 0.562 | 0.306 |
| 4 | 0.545 | 0.287 |
| Average | 0.564 ± 0.010 | 0.292 ± 0.010 |
| Coefficient of variance | 1.8% | 3.4% |

As is apparent from the results given in Table-C above, the method of this invention possesses an excellent reproducibility both in the case of using the standard Fg solution samples and in the case of using the actual body fluid (serum) samples.

EXAMPLE 3

To 5 ml of a glycine buffer solution, 100 mg of silica microparticles (prepared in the same manner as described in Example 1 of Japanese Patent Laying-Open Publication No. 120497/75) having an average diameter of 0.32 micron (although containing 15% of those particles having diameters of 0.5 micron or greater) are added and the mixture is subjected to ultrasonic vibrations of 28 KHz for an hour to form a suspension of silica microparticles.

An anti-Fg-antibody-sensitized silica suspension reagent is prepared in the same manner as described in Example 1, Part (1) except for using the silica microparticles-containing suspension thus prepared instead of the polystyrene latex with an average diameter of 0.481 micron used in Example 1, Part (1) and using another concentration of bovine serum albumin solution (0.05% concentration by weight).

Using the anti-Fg-sensitized silica suspension reagent, the absorbance is determined with each standard Fg solution in the same manner as described in Example 1, Part (2). The results are summarized in the following Table-D.

Table - D

| Concentration of standard Fg solution (μg/ml) | Absorbance at 1.2μ |
|---|---|
| 0.2 | 0.028 |
| 0.4 | 0.126 |
| 0.6 | 0.287 |
| 0.8 | 0.460 |
| 1.0 | 0.631 |

Figure 8:
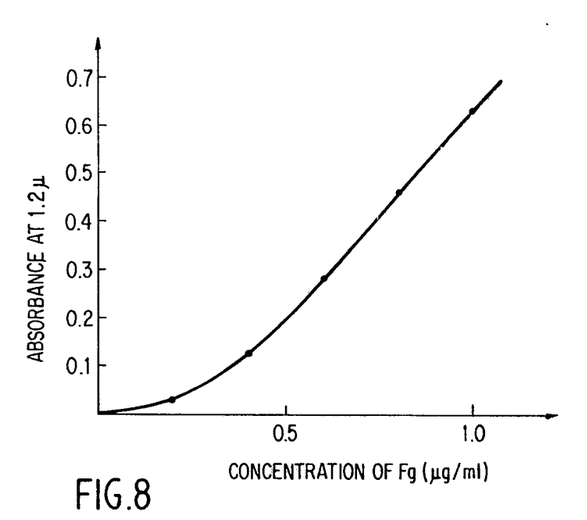
FIG. 8 shows a standard curve of absorbance measured at a wavelength of 1.2 microns using an anti-Fg-silica particles with an average diameter of 0.32 micron and a set of standard Fg solutions.

A standard curve is plotted from the above data as in Example 1, Part (2), said standard curve being shown in FIG. 8. It can be seen from FIG. 8 that a clean linear relationship is established between the concentration of Fg and the absorbance when the concentration of standard Fg solution is 0.4 μg/ml or higher.

Unknown samples (urine, serum and intrapleural fluid) collected from subjects are subjected to the same procedure as described in Example 1, Part (3) to determine Fg in the unknown samples. The results are summarized in the following Table-E.

Table - E

| Subject No. | Unknown sample Material | Dilution factor | Absorbance determined | Fg concentration in unknown sample (μg/ml) Method of this invention | RIA method |
|---|---|---|---|---|---|
| 1 | Urine | × 1 | 0.125 | 0.400 | 0.359 |
| 2 | " | × 10 | 0.210 | 5.000 | 5.117 |
| 3 | " | × 1 | 0.110 | 0.380 | 0.368 |
| 4 | Serum | × 1 | 0.440 | 0.770 | 0.800 |
| 5 | " | × 1 | 0.490 | 0.830 | 0.892 |
| 6 | Cancerous intrapleural fluid | × 400 | 0.211 | 200 | 197.4 |

EXAMPLE 4

The absorbance is determined at wavelengths of applied light of 1.2 and 1.7 microns in the same manner as described in Example 1, Parts (1) and (2), except for using a polystyrene latex with an average particle diameter of 0.804 micron (Dow Chemical Co., 10% solids content by weight) instead of the polystyrene latex with an average diameter of 0.481 micron (Dow Chemical Co.) and using another concentration of bovine serum albumin (0.1% concentration by weight). The results are given in the following Table-F.

Table - F

| Concentration of Standard Fg solution | Absorbance at | |
| --- | --- | --- |
| | 1.2 $\mu$ | 1.7 $\mu$ |
| 0.2 | 0.127 | 0.083 |
| 0.4 | 0.258 | 0.198 |
| 0.6 | 0.418 | 0.452 |
| 0.8 | 0.388 | 0.592 |
| 1.0 | 0.258 | 0.622 |

From the results shown in Table-F, it can be seen that a clear correlation is established between the concentration of Fg and the absorbance when the wavelength of the applied light is longer than the average diameter of the solid carrier particles (polystyrene latex particles) used by a factor exceeding 2.

EXAMPLE 5

Following the procedure as described in Example 1, Part (1), except that the anti-human fibrinogen antibody is replaced by anti-human chorionic gonadotropin antibody (anti-hCG) and the polystyrene latex with an average diameter of 0.481 micron by another polystyrene latex with an average particle diameter of 0.234 micron (Dow Chemical Co.), an anti-hCG-sensitized latex reagent is prepared. Using the anti-hCG-sensitized latex reagent thus obtained, the absorbance is determined at a wavelength of the applied light of 1.2 microns in the same manner as described in Example 1, Part (2), except for using a standard hCG solution instead of the standard Fg solution. The results are summarized in the following Table-G.

Table - G

| Concentration of standard hCG solution (IU/ml) | Absorbance at 1.2 microns |
| --- | --- |
| 0.1 | 0.048 |
| 0.2 | 0.130 |
| 0.3 | 0.168 |
| 0.4 | 0.261 |
| 0.5 | 0.360 |
| 0.7 | 0.630 |
| 1.0 | 0.972 |

A standard curve is prepared from the above data in the same manner as described in the foregoing. On the other hand, urine samples are collected from several subjects and subjected to the determination of urinary hCG in the same manner as described in Example 1, Part (3). The results are summarized in the following Table-H.

Table - H

| Subject No. | Unknown samples | | Absorbance determined | hCG concentration in unknown samples (IU/ml) | |
| --- | --- | --- | --- | --- | --- |
| | Material | Dilution factor | | Method of this invention | RIA method |
| 1 | Urine | × 1 | 0.400 | 0.564 | 0.482 |
| 2 | " | " | 1.122 | 0.966 | 1.120 |
| 3 | " | " | 0.955 | 0.944 | 0.857 |
| 4 | " | " | 0.990 | 0.952 | 0.925 |

EXAMPLE 6

In a glass absorption cell having a thickness of 2 mm equipped with an L-shaped stirring rod, 0.1 ml of the anti-Fg-sensitized latex reagent as prepared in Example 2 and 0.3 ml of one of standard Fg solutions having concentrations of Fg as indicated in Table-I below are placed, and the absorbance of the reaction mixture is monitored continuously at a wavelength of the applied light of 1.2 microns in the same manner as described in Example 1, Part (2) in order to read the time required for the absorbance to reach 0.5, while the stirring rod is moved up and down vertically at a definite speed of 200 vibrations per minute. The results are given in the following Table-I.

Table - I

| Concentration of standard Fg solution (mg/ml) | Time required to reach 0.5 in absorbance (sec.) |
| --- | --- |
| 2 | 26.9 |
| 4 | 11.3 |
| 6 | 6.4 |
| 8 | 4.7 |
| 10 | 2.9 |

Figure 9:
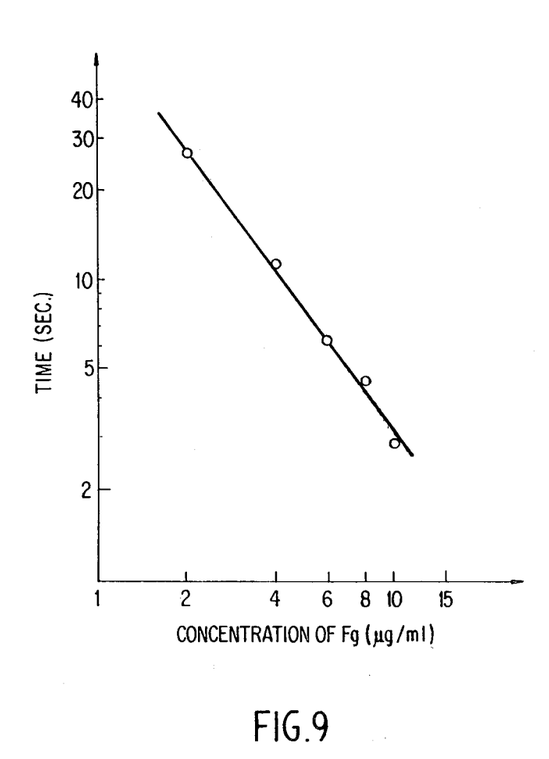
FIG. 9 shows a standard curve of time required for the absorbance at a wavelength of 1.2 microns to reach 0.5, when an anti-Fg-sensitized latex reagent is reacted with each of standard Fg solutions at various concentrations.

The above data are plotted on log-log graph paper with concentration of standard Fg solution as abscissa and time required to reach 0.5 in absorbance as ordinate to prepare a standard curve. The standard curve, as shown in FIG. 9, gives a clean straight line.

Then, 0.3 ml of any of unknown samples (urine, serum and intrapleural fluid) collected from different subjects and 0.1 ml of the above-mentioned anti-Fg-sensitized latex reagent are placed in a glass absorption cell having a thickness of 2 mm equipped with an L-shaped stirring rod and the time required for the absorbance to reach 0.5 is measured at a wavelength of the applied light of 1.2 microns in the same manner as above, whereupon the value of Fg concentration corresponding to the period of time measured is read from the standard curve as prepared in the above. The results are summarized in the following Table-J.

Table - J

| Subject No. | Unknown sample | | Time required to reach 0.5 in absorbance (sec.) | Fg concentration in unknown sample ($\mu$g/ml) | |
| --- | --- | --- | --- | --- | --- |
| | Material | Dilution factor | | Method of this invention | RIA method |
| 1 | Urine | × 1 | 9.2 | 4.5 | 5.117 |
| 2 | Cancerous intrapleural fluid | × 50 | 11 | 195 | 197.4 |
| 3 | Serum | × 1 | 25 | 2.1 | 2.210 |
| 4 | " | × 1 | 20 | 2.5 | 2.302 |
| 5 | " | × 1 | 3.8 | 8.6 | 9.020 |
| 6 | " | × 1 | 12 | 3.7 | 3.723 |

EXAMPLE 7

(1) Preparation of an oxytocin-sensitized latex reagent

One (1.0) ml of an oxytocin solution at a concentration of 220 IU/ml dissolved in aqueous 0.1 N acetic acid solution is mixed with 0.5 ml of a polystyrene latex with an average particle diameter of 0.481 micron (Dow Chemical Co., 10% solids content by weight), and the mixture is stirred at room temperature for 2 hours and then centrifuged (at 12,000 rpm) for 20 minutes under cooling at 2° to 4° C. The precipitates are separated by decantation and the collected oxytocin-sensitized latex particles are dispersed in 4 ml of an EDTA-glycine buffer solution containing 0.2% by weight bovine serum albumin to prepare an oxytocin-sensitized latex reagent which contains the latex particles at a concentration of 1% by weight.

(2) Decision of the optimum concentration of oxytocin antiserum

A 0.1 ml aliquot of the oxytocin-sensitized latex reagent as prepared in Part (1) is mixed with 0.1 ml of an isotonic sodium chloride solution and 0.2 ml of oxytocin antiserum which has been diluted with an isotonic sodium chloride solution by a factor indicated in Table-K below. The mixture is shaken on a reciprocal shaker at 200 strokes per minute for 12 minutes and the absorbance is determined at a wavelength of the applied light of 1.2 microns in the same manner as described in Example 1, Part (2). The results are given in the following Table-K.

Table - K

| Dilution factor of oxytocin antiserum | Absorbance at 1.2 $\mu$ |
|---|---|
| × 20 | 1.175 |
| × 30 | 0.618 |
| × 40 | 0.393 |
| × 50 | 0.327 |
| × 80 | 0.220 |
| ×100 | 0.162 |

From the above data, it is decided that the optimum concentration of the oxytocin antiserum resides in around a dilution factor of about 30.

(3) Preparation of a standard curve

In a plastic test tube, 0.2 ml of a solution prepared by diluting the oxytocin antiserum as used in Part (2) above by a factor of 30 and 0.1 ml of a standard oxytocin solution (dissolved in an aqueous 0.1 N acetic acid) at a concentration indicated in Table-L below are placed and thoroughly mixed. After the mixture is allowed to stand at room temperature for 30 minutes, 0.1 ml of the oxytocin-sensitized latex reagent as prepared in Part (1) above is added to the test tube and the resulting mixture is shaken on a reciprocal shaker at 200 strokes per minute for 12 minutes. The liqid thus obtained is placed in a glass absorption cell with a thickness of 2 mm and the absorbances is determined at a wavelength of the applied light of 1.2 microns in the same manner as described in Example 1, Part (2). The results are summarized in the following Table-L.

Table - L

| Concentration of standard oxytocin solution ($\mu$IU/ml) | Absorbance at 1.2$\mu$ | $\Delta$ D* |
|---|---|---|
| 2,000 | 0.395 | 0.183 |
| 1,500 | 0.450 | 0.128 |
| 1,000 | 0.483 | 0.095 |
| 500 | 0.525 | 0.053 |
| 300 | 0.550 | 0.028 |
| 0 | 0.578 | — |

*$\Delta$ D = (the absorbance at zero concentration of the standard oxytocin solution) minus (the absorbance at the indicated concentration of the same)

Figure 10:
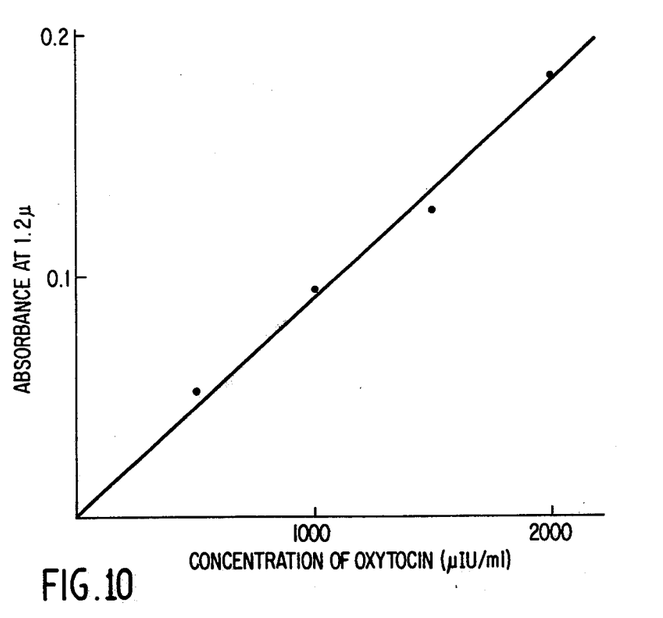
FIG. 10 shows a standard curve of absorbance measured at a wavelength of 1.2 microns after oxytocin antiserum is reacted with each of standard oxytocin solutions at various concentrations and oxytocin-sensitized latex particles are then added to the reaction mixture.

When the above data are plotted graphically with concentration of standard oxytocin solution as abscissa and D as ordinate, a clean linear relationship is established as shown in FIG. 10.

Using the standard curve thus prepared, it is possible to effect the determination of oxytocin in the serums of pregnant women.

EXAMPLE 8

(1) Preparation of an hCG-sensitized latex reagent

In 5 ml of 0.05 N hydrochloric acid, 7,900 IU/ml of human chorionic gonadotropin (hCG) is dissolved and hydrolyzed at 80° C for an hour. After the solution is subjected to dialysis and subsequent suction filtration, the hydrolyzed hCG thus obtained is dissolved in 2 ml of a 0.05 M borate buffer solution (pH 8.7) and diluted to 10 ml in the total volume.

A 5 ml aliquot of a 2% solution of a polystyrene latex (Dow Chemical Co., 10% solids content by weight) with an average particle diameter of 0.481 micron is gradually added to the hydrolyzed hCG solution under stirring. The resulting hCG-sensitized latex particles are centrifuged at 13,000 rpm for 20 minutes and the sensitized latex particles precipitated are separated and suspended in 10 ml of a 0.2% solution of bovine serum albumin in the borate buffer solution. The suspension is then centrifuged and the collected precipitates are centrifugally washed with the borate buffer solution and finally suspended in 10 ml of the buffer solution to provide an hCG-sensitized latex reagent containing 1% latex particles by weight.

(2) Preparation of a standard curve

The optimum concentration (i.e., dilution by a factor of 300 in this case) of anti-hCG serum is decided in the same manner as described in Example 7, Part (2). In a plastic test tube, 0.2 ml of an anti-hCG serum solution prepared by diluting the serum with an isotonic sodium chloride solution by a factor of 300 and 0.1 ml of a standard hCG solution at a concentration indicated in Table-M below are placed and shaken for 10 minutes. Subsequently 0.1 ml of the hCG-sensitized latex reagent as prepared in Part (1) above is added and the mixture is shaken for 10 minutes on a reciprocal shaker at 200 strokes per minute. The resulting liquid is placed in a glass absorption cell with a thickness of 2 mm and the absorbence is determined at a wavelength of the applied light of 1.0 micron in the same manner as described in the foregoing Example 1, Part (2). The results are given in the following Table-M.

Table / M

| Concentration of standard hCG solution (IU/ml) | Absorbance at 1.0$\mu$ |
|---|---|
| 10 | 0.140 |
| 1 | 0.208 |
| 0.1 | 0.271 |

Figures 11, 12:
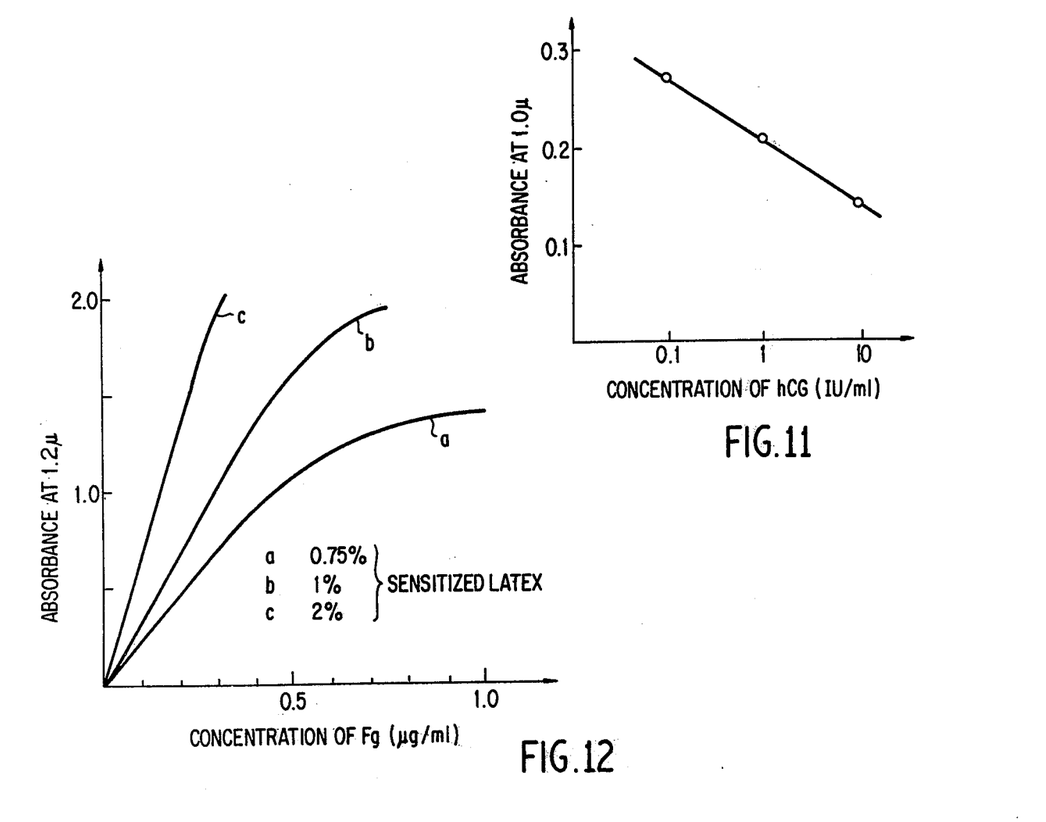
FIG. 11 shows a standard curve of absorbance measured at 1.0 micron after anti-hCG serum is reacted with each of standard hCG solutions at various concentrations and hCG-sensitized latexparticles are then added to the reaction mixture.
FIG. 12 is a graph which shows the change of detection sensitivity with concentration of anti-Fg-sensitized polystyrene latex.

When the above data are plotted graphically with logarithm of concentration of standard hCG solution as abscissa and absorbance as ordinate, the standard curve prepared gives a clean straight line, as shown in FIG. 11, in these concentrations at which the measurement is actually carried out.

Thus, it is possible to effect the determination of hCG in the serums of pregnant women using this standard curve.

EXAMPLE 9

In a plastic test tube, 0.1 ml of the anti-Fg-sensitized latex reagent as prepared in Example 1, Part (1) (the average diameter of the polystyrene latex particles: 0.481 micron; sensitized latex particles content: 1% by weight) and 0.3 ml of a standard Fg solution (dissolved in an isotonic sodium chloride solution containing 0.5% by weight bovine serum albumin) at a concentration indicated in Table-N below are mixed thoroughly and then shaken for 3 hours on a reciprocal shaker at 200 strokes per minute. Subsequently the absorbance is determined at a wavelength of the applied light of 1.2 microns in the same manner as described in Example 1, Part (2). The results are shown in the following Table-N.

Table - N

| Concentration of standard Fg solution (mg/ml) | Absorbance at $1.2\mu$ |
|---|---|
| 10 | 0.048 |
| 20 | 0.125 |
| 40 | 0.324 |
| 60 | 0.540 |
| 80 | 0.718 |
| 100 | 0.802 |

When a standard curve is prepared on the basis of the above data, a clear correlation is found between the concentration of the standard Fg solution and the absorbance. Thus, in accordance with the invention, it is possible to determine ultramicro amounts of Fg of the order of ng (nanograms)/ml, and such high sensitivity is comparable to that of the RIA method.

EXAMPLE 10

Anti-Fg-sensitized latex reagents containing the anti-Fg-sensitized latex particles at concentrations of 0.75%, 1.0% and 2.0% by weight, respectively, are prepared in the same manner as described in Example 1, Part (1), except for the use of another polystyrene latex with an average particle diameter of 0.35 micron. With each anti-Fg-sensitized latex reagent thus prepared, a standard curve is prepared in the same manner as described in Example 1, Part (2) (wavelength of the applied light 1.2 microns; shaking time 10 minutes). These standard curves are shown in FIG. 12. As is evident from FIG. 12, the detection sensitivity for Fg increases as the concentration of the sensitized latex particles in the anti-Fg-sensitized latex reagent becomes higher.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. An absorbance method of measuring antigens and antibodies comprising supporting an antibody or an antigen on insoluble carrier particles with an average diameter of not greater than 1.6 microns to sensitize the insoluble carrier particles, reacting the supported antibody and/or antigen with a corresponding antigen or antibody or a mixture thereof in a liquid medium, irradiating the reaction mixture with light having a wavelength in the range of 0.6 to 2.4 microns and longer than the average diameter of said carrier particles by a factor of at least 1.5 and measuring the absorbance of the reaction mixture.

2. The method according to claim 1 wherein the insoluble carrier particles used have an average diameter in the range of 0.1 to 1.0 micron.

3. The method according to claim 2 wherein the insoluble carrier particles used have an average diameter in the range of 0.2 to 0.8 micron.

4. The method according to claim 1 wherein said carrier particles consist essentially of fine powder of an organic high molecular substance or an inorganic substance which is substantially insoluble in the liquid medium.

5. The method according to claim 4 wherein said fine powder of the organic high molecular substance is a fine synthetic resin, bacteria or cell membrane fragments.

6. The method according to claim 4 wherein said fine powder of the organic high molecular substance is polystyrene latex particles.

7. The method according to claim 4 wherein said fine powder of the inorganic substance consists of at least one substance selected from the group consisting of metals, inorganic oxides or minerals.

8. The method according to claim 4 wherein said fine powder of inorganic substance is fine silica, alumina or silica-alumina.

9. The method according to claim 1 wherein the reaction of said antibody- or antigen-sensitized insoluble carrier particles with said antigen or antibody or a mixture thereof is carried out under conditions that accelerate contact of the carrier particles with each other as much as possible.

10. The method according to claim 9 wherein said reaction is carried out with agitation.

11. The method according to claim 1 wherein reaction of said antibody- or antigen-sensitized insoluble carrier particles with said antigen or antibody or a mixture thereof is carried out under specifically determined conditions which accelerate contact of the carrier particles with each other and the absorbance of the resulting reaction mixture is then measured.

12. The method according to claim 11 wherein said reaction is carried out with agitation.

13. The method according to claim 1 wherein the amount or concentration of the antigen or antibody or both in said test liquid is determined by reacting the antigen, antibody or both contained in said test liquid with the corresponding antibody and/or antigen supported or said carrier, for a prescribed period of time under specifically determined conditions, and thereafter measuring the absorbance of the reaction mixture.

14. The method according to claim 1 wherein the amount or concentration of the antigen or antibody or both in said test liquid is determined by reacting the antigen, antibody or both contained in said test liquid with the corresponding antibody and/or antigen supported on said carrier, under specifically determined conditions, and measuring a period of time required for the absorbance of the reaction mixture to reach a predetermined value.

15. The method according to claim 1 wherein the light applied has a wavelength in the range of 0.8 to 1.4 microns.

16. The method according to claim 15 wherein the light applied has a wavelength in the range of 1 to 1.4 microns.

17. The method according to claim 1 wherein the light applied has a wavelength longer than the average diameter of the carrier particles by a factor of at least 2.

18. The method according to claim 1 wherein said carrier particles are used in such a proportion that the concentration of the carrier in the reaction mixture is 0.1 to 1% by weight.

19. The method according to claim 18 wherein said carrier particles are used in such a proportion that the concentration of the carrier in the reaction mixture is 0.2 to 0.6% by weight.

20. The method according to claim 1 wherein said liquid medium is water or a mixture of water and a water-miscible organic solvent.

21. The method according to claim 1 wherein a diluted or undiluted test liquid containing an antigen or antibody is added to and reacted with a suspension of the carrier particles on which a particular antibody or antigen is supported.

22. The method according to claim 1 wherein at first an antigen or antibody is added to and reacted with a test liquid containing the antibody or antigen to be measured and subsequently a suspension of the insoluble carrier particles on which a particular antigen or antibody is supported is added to and reacted with the reaction mixture of the first reaction.

23. The method according to claim 1 wherein the antibody or antigen is supported on said insoluble carrier particles by physical and/or chemical adsorption thereon.

24. The method according to claim 1 wherein the antibody or antigen is supported on said insoluble carrier particles by chemical bonding therewith by the use of a coupling agent.

25. An apparatus for measuring antigens and antibodies, which comprises:
   an absorption cell holding the reaction mixture obtained by reacting an antibody or antigen supported on insoluble carrier particles having an average diameter of not greater than 1.6 microns, with a corresponding antigen or antibody or a mixture thereof in a liquid medium, said cell having a thickness of 0.5 to 4 mm; and said cell being in
   a photometer which comprises an irradiation unit for applying light of a particular wavelength to the cell and a detection unit for measuring the light absorbed by said cell; wherein said wavelength is selected from the range of 0.6 to 2.4 microns.

26. The apparatus according to claim 25 wherein the insoluble carrier particles have an average diameter in the range of 0.1 to 1.0 micron.

27. The apparatus according to claim 26 wherein the insoluble carrier particles have an average diameter in the range of 0.2 to 0.8 micron.

28. The apparatus according to claim 25 wherein the thickness of the cell is from 1 to 2.5 mm.

29. The apparatus according to claim 25 wherein the walls of the cell which transmit the light are composed of transparent glass or synthetic resin having at least 30% transmittance for light of 0.6 to 2.4 microns.

30. The apparatus according to claim 25 wherein the photometer involves an irradiation unit for applying light of a specific wavelength selected from the range of 0.8 to 1.4 microns.

31. The apparatus according to claim 30 wherein the photometer involves an irradiation unit for applying light of a specific wavelength selected from the range of 1.0 to 1.4 microns.

32. The apparatus according to claim 25 wherein the cell is equipped with an agitator.

33. The apparatus according to claim 32 wherein the agitator comprises a mixing rod moving in the cell.

* * * * *